US008546566B2

(12) United States Patent
Schnaubelt et al.

(10) Patent No.: US 8,546,566 B2
(45) Date of Patent: Oct. 1, 2013

(54) PROCESS FOR MANUFACTURING DIHYDROPTERIDINONES AND INTERMEDIATES THEREOF

(75) Inventors: Juergen Schnaubelt, Oberhoefen/Warthausen (DE); Rolf Herter, Biberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 44 days.

(21) Appl. No.: 13/233,066

(22) Filed: Sep. 15, 2011

(65) Prior Publication Data
US 2012/0238754 A1    Sep. 20, 2012

(30) Foreign Application Priority Data
Oct. 12, 2010  (EP) .................................... 10187194

(51) Int. Cl.
*C07D 475/04* (2006.01)
(52) U.S. Cl.
USPC .......................................... 544/258; 544/403
(58) Field of Classification Search
USPC ................................................ 544/258, 403
See application file for complete search history.

(56) References Cited

U.S. PATENT DOCUMENTS

| 4,870,175 | A  | 9/1989  | Suzuki et al. |
| 4,957,922 | A  | 9/1990  | Lammens et al. |
| 5,043,270 | A  | 8/1991  | Abrams et al. |
| 5,167,949 | A  | 12/1992 | Ferrand et al. |
| 5,198,547 | A  | 3/1993  | Bailey et al. |
| 5,424,311 | A  | 6/1995  | Billhardt-Troughton et al. |
| 5,698,556 | A  | 12/1997 | Chan |
| 6,096,924 | A  | 8/2000  | Studer et al. |
| 6,156,766 | A  | 12/2000 | Arita et al. |
| 6,174,895 | B1 | 1/2001  | Kleinman |
| 6,605,255 | B2 | 8/2003  | Kroll et al. |
| 6,806,272 | B2 | 10/2004 | Bauer et al. |
| 6,861,422 | B2 | 3/2005  | Hoffmann et al. |
| 6,875,868 | B2 | 4/2005  | Bonnert et al. |
| 6,960,589 | B2 | 11/2005 | Cowart et al. |
| 7,238,807 | B2 | 7/2007  | Duran et al. |
| 7,241,889 | B2 | 7/2007  | Hoffmann et al. |
| 7,332,491 | B2 | 2/2008  | Grauert et al. |
| 7,371,753 | B2 | 5/2008  | Stadtmueller et al. |
| 7,414,053 | B2 | 8/2008  | Grauert et al. |
| 7,439,358 | B2 | 10/2008 | Linz et al. |
| 7,547,780 | B2 | 6/2009  | Grauert et al. |
| 7,625,899 | B2 | 12/2009 | Hoffmann et al. |
| 7,626,019 | B2 | 12/2009 | Duran et al. |
| 7,629,460 | B2 | 12/2009 | Grauert et al. |
| 7,638,627 | B2 | 12/2009 | Kankan et al. |
| 7,700,769 | B2 | 4/2010  | Grauert et al. |
| 7,723,517 | B2 | 5/2010  | Grauert et al. |
| 7,728,134 | B2 | 6/2010  | Linz et al. |
| 7,750,152 | B2 | 7/2010  | Hoffman et al. |
| 7,759,347 | B2 | 7/2010  | Hoffmann |
| 7,759,485 | B2 | 7/2010  | Linz et al. |
| 7,807,831 | B2 | 10/2010 | Grauert et al. |
| 7,816,530 | B2 | 10/2010 | Grauert |
| 8,003,786 | B2 | 8/2011  | Hoffmann et al. |
| 8,034,816 | B2 | 10/2011 | Linz et al. |
| 8,058,270 | B2 | 11/2011 | Munzert et al. |
| 8,138,341 | B2 | 3/2012  | Linz et al. |
| 8,138,373 | B2 | 3/2012  | Linz et al. |
| 8,143,247 | B2 | 3/2012  | Munzert et al. |
| 8,188,086 | B2 | 5/2012  | Linz et al. |
| 8,193,188 | B2 | 6/2012  | Hoffmann et al. |
| 8,202,867 | B2 | 6/2012  | Linz et al. |
| 8,329,695 | B2 | 12/2012 | Linz et al. |
| 2002/0183292 | A1 | 12/2002 | Pairet et al. |
| 2002/0183293 | A1 | 12/2002 | Banerjee et al. |
| 2003/0130286 | A1 | 7/2003  | Denny et al. |
| 2003/0162790 | A1 | 8/2003  | Cowart et al. |
| 2004/0024205 | A1 | 2/2004  | Borredon et al. |
| 2004/0029885 | A1 | 2/2004  | Bauer et al. |
| 2004/0127504 | A1 | 7/2004  | Cowart et al. |
| 2004/0147524 | A1 | 7/2004  | Bauer et al. |
| 2004/0176380 | A1 | 9/2004  | Hoffmann et al. |
| 2005/0014760 | A1 | 1/2005  | Hoffmann et al. |
| 2005/0014761 | A1 | 1/2005  | Hoffmann et al. |
| 2005/0148501 | A1 | 7/2005  | Palmer et al. |
| 2005/0159414 | A1 | 7/2005  | Nickolaus et al. |
| 2005/0165010 | A1 | 7/2005  | Nickolaus et al. |
| 2006/0004014 | A1 | 1/2006  | Hoffmann et al. |
| 2006/0009457 | A1 | 1/2006  | Hoffmann et al. |
| 2006/0025411 | A1 | 2/2006  | Hoffmann et al. |

(Continued)

FOREIGN PATENT DOCUMENTS

| CA | 2458699 A1 | 3/2003 |
| CA | 2517020 A1 | 9/2004 |

(Continued)

OTHER PUBLICATIONS

Rylander, P.N., "Hydrogenation Methods". 1985, Chapters 1, 2.

(Continued)

*Primary Examiner* — Bruck Kifle
(74) *Attorney, Agent, or Firm* — Michael P. Morris; Anthony P. Bottino

(57) ABSTRACT

The present invention relates to an improved process for manufacturing dihydropteridinones of general formula (12)

(11)

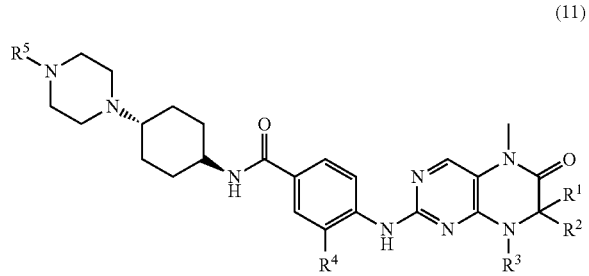

as well as intermediates thereof, wherein the groups $R^1$, $R^2$, $R^3$, $R^4$, and $R^5$ have the meanings given in the claims and specification.

13 Claims, No Drawings

(56) References Cited

U.S. PATENT DOCUMENTS

| | | |
|---|---|---|
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0043055 A1 | 2/2007 | Maier et al. |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0029990 A1 | 1/2009 | Maier et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2010/0029642 A1 | 2/2010 | Hoffmann et al. |
| 2010/0179134 A1 | 7/2010 | Singh et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |
| 2012/0107312 A1 | 5/2012 | Munzert et al. |
| 2012/0214995 A1 | 8/2012 | Linz et al. |
| 2012/0238754 A1 | 9/2012 | Schnaubelt et al. |
| 2012/0295864 A1 | 11/2012 | Taube et al. |
| 2012/0296091 A1 | 11/2012 | Sieger et al. |
| 2012/0329803 A1 | 12/2012 | Linz et al. |
| 2013/0012465 A1 | 1/2013 | Haslinger et al. |

FOREIGN PATENT DOCUMENTS

| | | |
|---|---|---|
| CA | 2517010 A1 | 11/2004 |
| CA | 2576290 A1 | 2/2006 |
| EP | 143478 A1 | 6/1985 |
| EP | 347146 A2 | 12/1989 |
| EP | 399856 A1 | 11/1990 |
| EP | 429149 A1 | 5/1991 |
| ES | 2287583 | 12/2007 |
| JP | 2009169737 A | 6/1997 |
| RU | 2002125451 A | 1/2004 |
| WO | 9608537 A1 | 3/1996 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 0119825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A1 | 10/2002 |
| WO | 03020722 A1 | 3/2003 |
| WO | 03093249 A1 | 11/2003 |
| WO | 2004014899 A1 | 2/2004 |
| WO | 2004076454 A1 | 9/2004 |
| WO | 2004093848 A2 | 11/2004 |
| WO | 2005067935 A1 | 7/2005 |
| WO | 2006005510 A1 | 1/2006 |
| WO | 2006018182 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2006021379 A1 | 3/2006 |
| WO | 2006021547 A1 | 3/2006 |
| WO | 2007014838 A1 | 2/2007 |
| WO | 2007054551 A1 | 5/2007 |
| WO | 2007090844 A1 | 8/2007 |
| WO | 2009019205 A1 | 2/2009 |
| WO | 2009112524 A1 | 9/2009 |
| WO | 2011101369 A1 | 8/2011 |
| WO | 2012049153 A1 | 4/2012 |
| WO | 2012156283 A1 | 11/2012 |
| WO | 2012156380 A1 | 11/2012 |

OTHER PUBLICATIONS

Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.

Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.

Science, vol. 310, Oct. 21, 2005, p. 409, Chemistry: One After Another.

Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.

Souillac, P. et al., "Characterization of delivery systems, differential scanning calorimetry". (In Encyclopedia of Controlled Drug Delivery), 1999, John Wiley & Sons, pp. 212-227.

Sugar, a. M. et al., "Comparison of three methods of antifungal susceptibility testing with the proposed NCCLS standard broth macrodilution assay: lack of effect of phenol red". Mycology, Diagn Microbiol. Infect. Dis. 1995, 21- pp. 129-133.

Takai, N. et al., "Polo-like kinases (PLKs) and cancer". Oncogene, 2005, 24, pp. 287-291.

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

Turner, S., "The Design of Organic Syntheses". Elsevier, 1976, pp. 10 and 149.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Visiting Nurse Association of America. www.vnaa.org/gen/Germ_Protection_Center_Cold_and_Flu_Resources,html, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

Wagner G.et al., "Synthesis of new phrido[3',2':4,5] thieno '3,2-d] 1,2,3-triazine derivatives as antianaphylactics".Biosciences Dept of the University of Leipzig, Pharmazie (Pharmacy), 48, vol. 7, 1993, pp. 514-518.

Webster's Comprehensive Dictionary, 1996, pp. 1013-1014.

Wikipedia. "Melting Point", Jan 17, 2007. http://en.wikipedia.org/wiki/Melting_point.
Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.
ACPS Meeting, Background Information. "Scientific considerations of plymorphism in pharmaceutical solids: abbreviated new drug applications". Oct. 2002.
Ahlenius, T. List of cardiovascular disorder/diseases. Ahlenius, Karolinska Institutet. Stockholm, Sweden. Cardiovascular Diseases, p. 1-34, Apr. 2007.
Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.
Arnold, K. "Collaboration to play key role in NCI's future, director says". Journal of the National Cancer Institute, Jun. 5, 2002, pp. 790-792, vol. 94, No. 11.
BBC News/Health, Killer Breast Cancern Therapy Hope, www.newsvote.bbc/co./uk, Published Jan. 21, 2006.
Bennett, J.C., et al., "Textbook of Medicine", Part XIV, Oncology, 1997.
Beshore, D.C.et al., "Preparation of Substituted Piperazinones via Tandem Reductive Amination-N.N-Acyl Transfer)-Cyclization". Organic Letters, 2002, vol. 4, No. 7, p. 1201-1204.
Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.
Chen, J.X. et al., "Parallel differentiated recognition of ketones and acetals". Angewandte Chemie Int. Ed, vol. 37, Issue 1/2, p. 91-93, 1998.
Dipolar aprotic solvent. Exhibit A, IUPAC Compendium of Chemical Terminology, 2nd Edition, 1997.
Doerwald, F.Z. Book Wiley-VCH Verlag GmbH & Co. KGaA, "Side reactions in organice synthesis: A Guide to Successful Synthesis Design". 2005.
Dyson, G, et al. "The Chemistry of Synthetic Drugs". 1964, p. 12-19.
Eurasian Opinion, Appin No. 2007/00389/28, Maly Slatoustinsky per., d.10, kv.15, 101000 Moscow, Russia, "EVRPOMARKPAT", 2007.
Ferrand, G., et al., "Synthesis and potential antiallergic activity of new pteridinones and related compounds". Eur. J. Med. Chem, 31, 1996, pp. 273-280. XP-2246920.
Ghandi, L, et al., "An Open-Label Phase II Trial of the PLK Inhibitor BI 2536 in Patients with Sensitive Relapse Small Cell Lung Cancer". ASCO Meeting 2009.
Giron, G. "Thernal analysis and calorimetric methods in the characterization of plymorphs and solvates". Thermochimica Acta 248, 1995, pp. 1-59.
Goodman-Gilman's "The Pharmacological Basis of Therapeutics". Ninth edition, 1996, pp. 1225-1271.
Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.
Jamieson, C. et al., "Application of ReactArray Robotics and Design of Experiments Techniques in Optimisation of Supported Reagent Chemistry". Org. Proc. Res. & Dev., 2002, 6, p. 823-825.
Jaworska, J., et al., "Review of methods for assessing the applicability domains of SARS and QSARS". Sponsor: The European Commission—Joint Research Ctr., Institute for Health and Consumer Protection—ECVAM, Italy, 2004.
Kashima, M. K. et al., "Expression of polo-like kinase (PLK1) in non-Hodgkin's lymphomas". NCBI, PubMed, 2005.
Kimball, S. D. et al., "Cell cycle kinases and checkpoint regulation in cancer". Annual Reports in Medicinal Chemistry, 36, Chapter 14, 2001, pp. 139-148.
Krause, M. et al., "Combination of Radiation and Polo-like Kinase 1 Inhibition with BI 6727 in tumour model A431". Strahlenther Onkol, 187, S1, 53 (v17-6), 2011.
Kummer B, et al., "Combination of Radiation and Polo-like Kinase 1 Inhibition with BI6727 in tumour model A431". Vortrag. 20. Symposium „Experimentelle Strahlentherapie and klinische Strahlenbiologie, Exp. Strahlenther. Klin. Strahlenbiol. 20: 93-96 (2011) (Lecture 20, Symposium Experimental Radiation Therapy and Clinical Radiation Biology.).
Kummer, B. et al., Presentation: "Combination of irradiation and polo-like kinase 1 inhibition with BI 6727 in tumour model a 431". OncoRay—National Centre for Radiation Research in Oncology, Dresden 2011, Experimental Radiotherapy and Clinical Radiobiology.
Leukemia & Lymphoma Society—Disease Information—Lymphoma. www.leukemia-lymphoma.org/all_page?item_id-7030, 2008.
Leukemia & Lymphoma Society—Disease Information. www.leukemia-lymphoma.org/all_page?item_id-7026, 2008.
Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.
Mashkovkii, M.D., "Medicaments". Moscow, Novaja Volna, 2001, vol. 1, p. 11.
Mashkovskii, M.D. "Drugs", Handbook for Doctors, 1993, Part I, Ch.1, p. 8.
Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.
Mayer, Sf, et al., "Enzyme-initiated domino (cascase) reactions". Chem. Soc. Rev, 2001, p. 332-339.
MedlinePlus: Bacterial Infections. www.nim.nih.gov/medlineplus/print/bacterialinfections.htm, date last updated Mar. 25, 2009.
MedlinePlus: Viral Infections. www.nim.nih.gov/medlineplus/print/viralinfections.htm, date last updated Feb. 11, 2009.
Merck Manual of Medical Information—Home Edition, Section 17. "Parasitic Infections". Chapter 184, 2003.
Mikhailov, I.B., Principles of Rational Pharmacotherapy. Handbook for clinical pharmacology for students of pediatric and medical faculties of medical high schools, St. Petersburg, Russia, "Foliant", 1999, p. 25.
Mito, K., et al., "Expression of polo-like kinase (PLK1) in non-Hodgkin's lymphomas". NCBI, PubMed, 2005, Leuk. Lymphoma, 46(2), pp. 251-231.
Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
Neidle, S. ed., "Cancer Drug Design and Discovery", Elsevier/Academic Press, 2008, p. 427-431.
Norman, P. "PDE4 inhibitors". Ashley Publications Ltd., Expert Opinions Ther. Patents, 1999, pp. 1101-1118.
Office Action mailed Dec. 10, 2003 for U.S. Appl. No. 10/226,710, filed Aug. 23, 2002. Inventor: Eckhart Bauer.
Office Action mailed Apr. 28, 2004 for U.S. Appl. No. 10/374,876, filed Feb. 26, 2003 Inventor: Matthias Hoffmann.
Ohio Dept of Health, "Brain and Other Central Nervous System Cancer in Ohio, 1997-2001". Sep. 2004, pp. 1-4.
Organic Chemistry, Grupo Editorial Iberoamerica, Section 13, 3, pp. 301-302, 1983 (best available in Spanish).
Rocha Lima, C.M. et al. "Randomized phase II trial of gemcitabine plus irinotecan or docetaxel uin stage IIIB or stage IV NSCLC" Annals of Oncology, 15(3), p. 410-418, 2004.
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
Rylander, P.N. "Hydrgenation Methods". 1985, Chapter 5, 6, 7.
Bug, G. et al., "Phase I/II Study of BI6727 (volasertib), An Intravenous Polo-Like Kinase-1 (Plkl) Inhibitor, in Patients with Acute Myeloid Leukemia (AML): Results of the Dose Finding for BI 6727 in Combination with Low-dose Cytarabine". Blood, vol. 116, No. 21, Nov. 19, 2010, p. 1359, American Socieity of Hematology (ASH); Orlando, FL, Dec. 2010.
International Search Report and Written Opinion for PCT/EP2011/067696 mailed Nov. 4, 2011.
Rudolph, D. et al., "430 Poster Characterization of BI 6727, a novel Polo-like kinase inhibitor with a distinct pharmacokinetic profile and efficacy in a model of taxane-resistant colon cancer". European Journal of Cancer. Supplement, Pergamon, Oxford, GB, vol. 6, No. 12, Oct. 1, 2008, p. 135. [retrieved on Oct. 1, 2008].

International Search Report and Written Opinion for PCT/EP2012/058704 mailed Aug. 8, 2012.

Schoffski, P., "Polo-like kinase (PLK) inhibitors in preclinical and early clinical development in oncology", The Oncologist, vol. 14, 2009, pp. 559-570.

Schoffski, P., et al., "A phase I single dose escalation study of the novel polo-like kinase 1 inhibitor BI 6727 in patients with advanced solid tumours", EJC Supplement, vol. 6. No. 12, Oct. 2008, p. 14-15.

Clinical Trials: NCT01348347. BI6727 (Volasertib) Monotherapy Phase I Trial in Japanese Patients with Advanced Soliid Tumours. Apr. 29, 2011 [Retrieved from the Internet: URL: http://www.clinicaltrials.gov./ct2/show/NCT01348347?term=volasertib&rank=1] retrieved Jul. 16, 2012.

International Search Report and Written Opinion for PCT/EP2011/052280 mailed Apr. 29, 2011.

Abstract in English for JP09169737, Date of Publication: Jun. 30, 1997, Applicant Tosoh Corp, Inventor: K. Hiroyuki, Title: Production of N-Methylimidazoles. Date filed: Dec. 21, 1995.

X-ray Diffraction—Factors that affect d's and l's. [Downloaded from the internet Mar. 9, 2011, URL: http://www.gly.uga.edu/Schroeder/geol6550/XRD.html].

Gould, P. L., "Salt selection for basic drugs", International Journal of Pharmaceutics, 33(1986), 201-217.

Neau, S. H., Pharmaceutical Salts, CRC Press, 2008, Ch 17, p. 417-435.

Bastin, R. J. et al., "Salt Selection and Optimisation Procedures for Pharmaceutical New Chemical Entities", Organic Process Research and Development, 2000, 4,427-435.

Morris, K.R. et al., "An integrated approach to the selection of optimal salt form for a new drug candidate", International Journal of Pharmaceutics, 105, 1994, 209-217.

Badawy, S. I. et al., "Sale Selection for Phamaceutical Compounds", Preformulation in Solid Dosage Form Develolpment, Infoa Healthcare 2008, Chapter 2.3, 63-80.

Serajuddin, Abu T.M., "Salt formation to improve durg solubility", Advanced Drug Delivery Reviews, 59, 2007, 603-616.

"Salt Forms of Drug Absorption", Swarbrick, et al. editors, Encyclopedia of Pharm. Tech. 13 Marcel Dekker, NY, 1996, 453-499.

Goodman and Gilman 9th Edition; 1996; pp. 1225-1232 and 1269-1271.

Medema et al.; Polo-like Kinase 1 Inhibitors and Their Potential Role in Anticancer Therapy, with a Focus on NSCL; Clinical Cancer Research; 2011; vol. 17; No. 20; pp. 6459-6466.

Schoffski et al., Polo-Like Kinase (PLK) Inhibitors in Preclinical and Early Clinical Development in Oncology, The Oncologist, 2009, 14:559-570.

Rudolph et al., BI 6727, a Polo-like kinase inhibitor with improved pharmacokinetic profile and broad antitumor activity, Clinical Cancer Research, 2009.

PROCESS FOR MANUFACTURING DIHYDROPTERIDINONES AND INTERMEDIATES THEREOF

The present invention relates to a process for manufacturing dihydropteridinones of general formula (11)

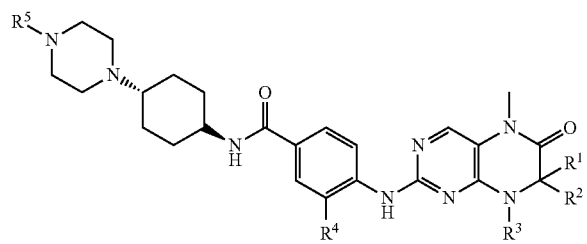
(11)

wherein the groups $R^1$, $R^2$, $R^3$, $R^4$, and $R^5$ have the meanings given in the claims and specification, as well as related intermediates thereof, optionally in form of the tautomers, racemates, enantiomers, diastereomers and the mixtures thereof and optionally the salts thereof.

BACKGROUND OF THE INVENTION

Pteridinone and pteridinone derivatives are known in prior art as active substances with an antiproliferative activity, particularly for the treatment of diseases comprising an abnormal cell proliferation by inhibition of polo-like kinases as mitotic regulators, especially in case the polo-like kinase is PLK-1, preferably for the treatment and/or prevention of cancer, infections, inflammatory and autoimmune diseases.

For example, WO 01/019825 A1 discloses specific pteridinones which are described to be potent inhibitors of cyclin-dependent kinases (cdks) and growth-factor-mediated kinases and are used for the treatment of cell proliferative diseases and disorders, particularly tumour and viral diseases. Also WO 03/020711 discloses the use of dihydropteridinone derivatives for the treatment of tumoral diseases. Further, WO 2006/018185 A2 is related to the use of dihydropteridinones in the cancer therapy.

Also a number of manufacturing processes of pteridones is described in prior art:

For example, WO 2004/076454 A1 and WO 2006/018220 disclose specific dihydropteridinones, methods for the production and use thereof.

Nevertheless, there exists a need for an improved method of manufacturing dihydropteridinones which overcomes the above described deficiencies. The object of the present invention is therefore to provide a method according to which dihydropteridinones may be provided in a high yield with improved high purities which may be readily conducted in large-scale.

DETAILED DESCRIPTION OF THE INVENTION

The present invention relates to a process of manufacturing dihydropteridinones and related intermediates thereof.

According to the present invention the produced compounds of general formula (11) are as follows:

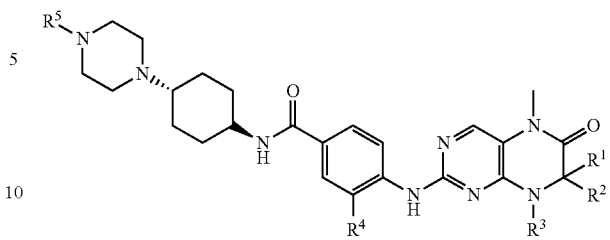
(11)

wherein $R^1$ and $R^2$ denote independently from each other a hydrogen or $C_1$-$C_6$-alkyl, $R^3$ denotes hydrogen or a group selected from $C_1$-$C_6$-alkyl and $C_3$-$C_8$-cycloalkyl, $R^4$ denotes hydrogen or a group selected from among —CN, hydroxy, $C_1$-$C_6$-alkyl, $C_1$-$C_3$-alkyloxy and $C_1$-$C_6$-alkylthio, $R^5$ denotes $C_1$-$C_6$-alkyl, $C_1$-$C_4$-alkyl-$C_3$-$C_8$-cycloalkyl or $C_3$-$C_8$-cycloalkyl, optionally in the form of the tautomers, the racemates, the enantiomers, the diastereomers and the mixtures thereof, and optionally the salts thereof.

The process according to the present invention may provide a single step process (step 1, or step 2 or step 3) or may provide combinations of steps in a multi-stage process, the process steps and compounds which may be manufactured according to the processes according to the present invention are as follows:

The present invention relates to a process (step 1) for manufacturing a compound of formula (5)

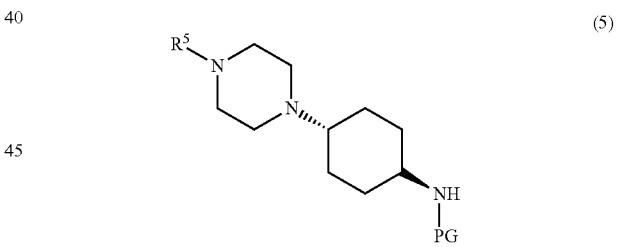
(5)

wherein $R^5$ denotes $C_1$-$C_6$-alkyl, $C_1$-$C_4$-alkyl-$C_3$-$C_{10}$-cycloalkyl or $C_3$-$C_{10}$-cycloalkyl, characterised in that a compound of formula (3)

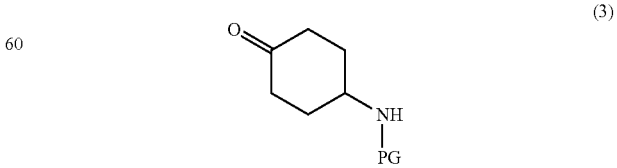
(3)

wherein PG is a protecting group is reacted with a compound of general formula (4)

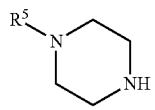
(4)

wherein
$R^5$ is as hereinbefore defined,
via an enamine intermediate which is hydrogenated in the presence of a metal catalyst like Ni, Pd, Pt and a solvent or a mixture of solvents. Preferred catalysts are Pt/C and platinum-IV-oxide ($PtO_2$). Most preferred is platinum-IV-oxide ($PtO_2$). The solvent is preferably an aprotic organic solvent or an alcohol or a mixture of an aprotic solvent and an alcohol. Particularly use is made of a toluene/ethanol mixture.

The present invention relates also to a process (step 2) for manufacturing a compound of formula (6)

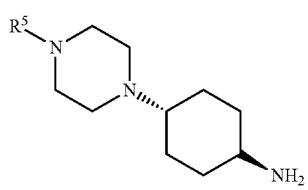
(6)

wherein
$R^5$ is as hereinbefore defined, characterised in that
the protecting group PG in a compound of general formula (5)

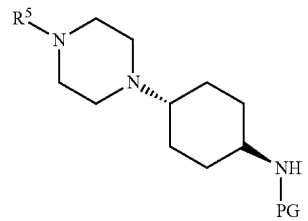
(5)

wherein
$R^5$ and PG are as hereinbefore and hereinafter defined,
is removed by acidic hydrolysis using p-toluenesulfonic acid (TsOH) as non-nucleophilic acidic reagent for cleavage of the protecting group.

The present invention also relates to a process (step 3) for manufacturing a compound of formula (8)

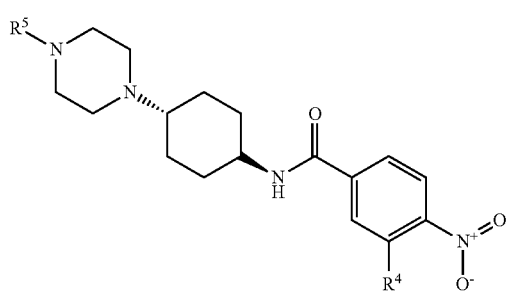
(8)

wherein
$R^5$ is as hereinbefore defined,
$R^4$ denotes hydrogen or a group selected from among —CN, hydroxy, $C_1$-$C_6$-alkyl, $C_1$-$C_5$-alkyloxy and $C_1$-$C_6$-alkylthio,
characterised in that
a compound of general formula (7)

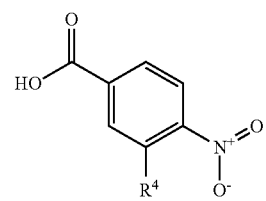
(7)

wherein
$R^4$ is as hereinbefore defined, optionally converted into an acyl halide compound, is reacted with the amine compound of formula (6)

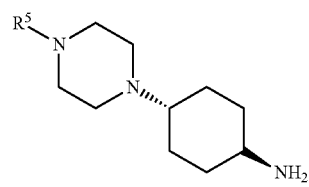
(6)

wherein
$R^5$ is as hereinbefore defined,
using an alkali or alkaline earth hydroxide, preferably NaOH or KOH, as base and a protic solvent, preferably water.

The present invention also relates to a process (step 1 to step 5) for manufacturing a compound of formula (11)

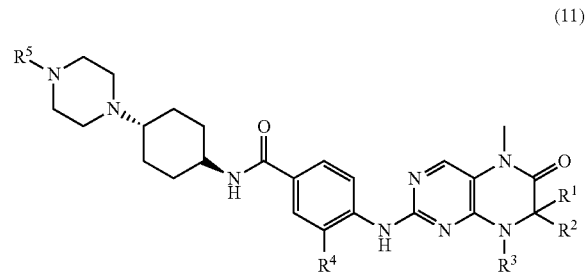
(11)

wherein
R¹ to R⁵ are as hereinbefore defined,
comprising the following steps:
Step 1:
A Compound of Formula (3)

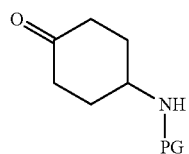

(3)

wherein PG is a protecting group
is reacted with a compound of general formula (4)

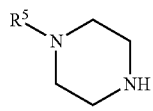

(4)

wherein
R⁵ is as hereinbefore defined,
via an enamine intermediate which is hydrogenated in the presence of a metal catalyst, preferably, a Pt catalyst and a solvent or a mixture of solvents;
to obtain a compound of formula (5)

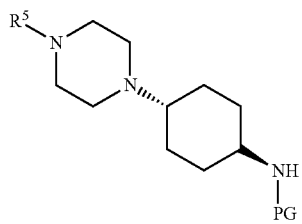

(5)

wherein R⁵ and PG are as hereinbefore and hereinafter defined;
Step 2:
In a Compound of Formula (5) as Hereinbefore Defined, the protecting group PG is removed by acidic hydrolysis using p-toluenesulfonic acid (TsOH) as non-nucleophilic acidic reagent for cleavage of the protecting group
to obtain a compound of formula (6)

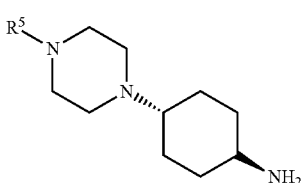

(6)

wherein
R⁵ is as hereinbefore defined;
Step 3:
A Compound of General Formula (7)

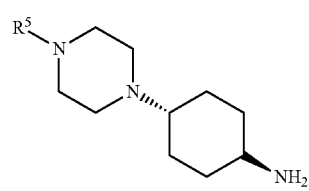

(7)

wherein
R⁴ is as hereinbefore defined, optionally converted into an acyl halide compound, is reacted with the amine compound of formula (6)

(6)

wherein
R⁵ is as hereinbefore defined,
using an alkali or alkaline earth hydroxide, preferably NaOH or KOH, as base and a protic solvent, preferably water,
to obtain a compound of formula (8)

(8)

wherein
R⁴ and R⁵ are as hereinbefore defined;
Step 4:
A Compound of General Formula (8) as Hereinbefore Defined
is hydrogenated to obtain a compound of formula (9)

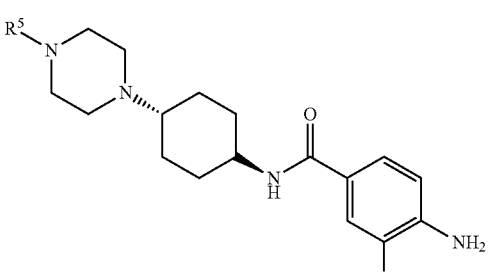

(9)

wherein

R⁴ and R⁵ are as hereinbefore defined;

Step 5:

A Compound of Formula (9) as Hereinbefore Defined, is reacted with a compound of formula (10)

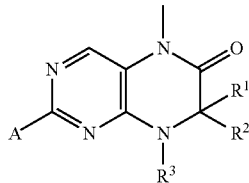
(10)

wherein R¹, R² and R³ are as hereinbefore defined and A is a leaving group, to obtain a compound of formula (11)

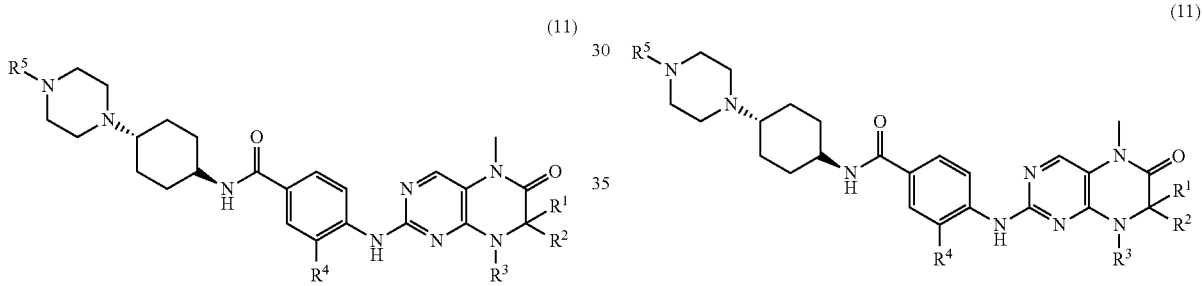
(11)

wherein

R¹ to R⁵ are as hereinbefore defined.

The present invention also relates to a process for manufacturing a compound of formula (9)

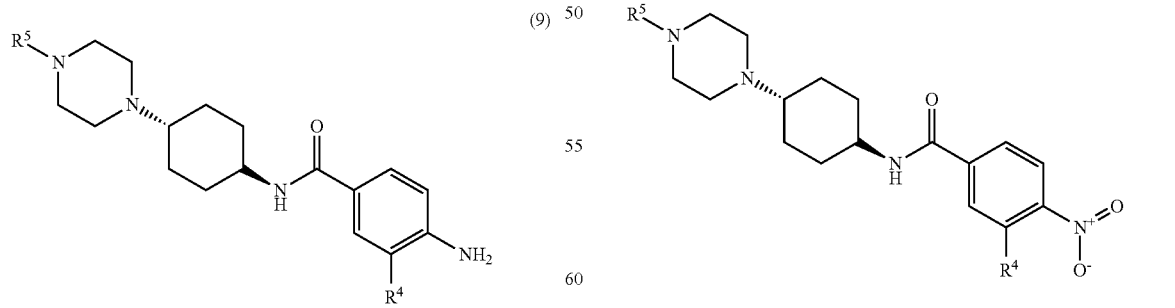
(9)

wherein

R⁴ and R⁵ are as hereinbefore defined, using process step 1 and/or process step 2 and/or process step 3 as hereinbefore defined.

The present invention also relates to a process for manufacturing a compound of formula (11)

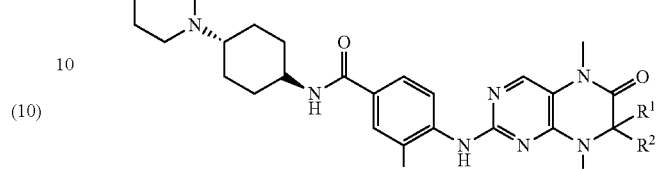
(11)

wherein

R¹ to R⁵ are as hereinbefore defined, using process step 1 and/or process step 2 and/or process step 3 as hereinbefore defined.

The present invention also relates to a process for manufacturing a compound of formula (11)

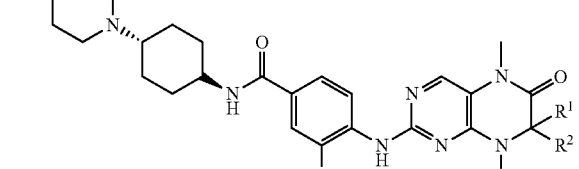
(11)

wherein

R¹ to R⁵ are as hereinbefore defined using a compound of formula (8)

(8)

wherein

R⁴ and R⁵ are as hereinbefore defined, wherein the compound of formula (8) is obtained using process step 1 and/or process step 2 and/or process step 3 as hereinbefore defined;

or
using a compound of formula (9)

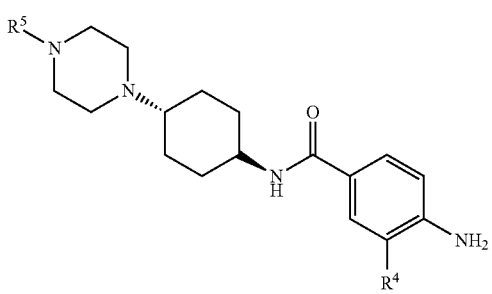
(9)

wherein
R⁴ and R⁵ are as hereinbefore defined,
wherein the compound of formula (9) is obtained using process step 1 and/or process step 2 and/or process step 3 as hereinbefore defined.

The present invention also relates to a process (step 4) for manufacturing a compound of formula (9)

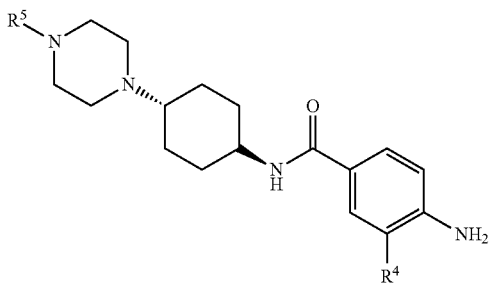
(9)

wherein
R⁴ and R⁵ are as hereinbefore defined, characterised in that a compound of general formula (8)

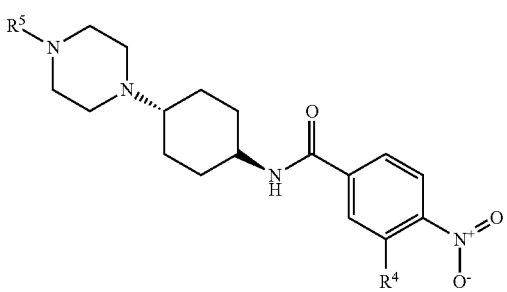
(8)

wherein
R⁴ and R⁵ are as hereinbefore defined,
is hydrogenated,
wherein the compound of formula (8) is obtained using process step 1 and/or process step 2 and/or process step 3 as hereinbefore defined.

The present invention also relates to a process (step 5) for manufacturing a compound of formula (11)

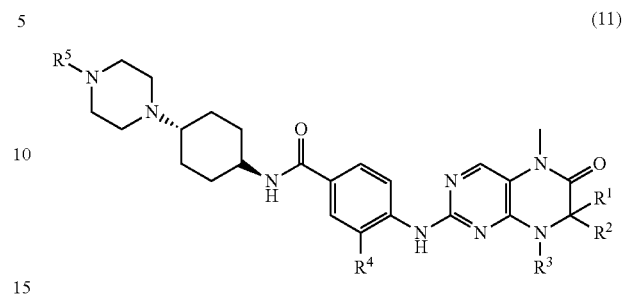
(11)

wherein
R¹ to R⁵ are as hereinbefore defined,
wherein a compound of formula (9)

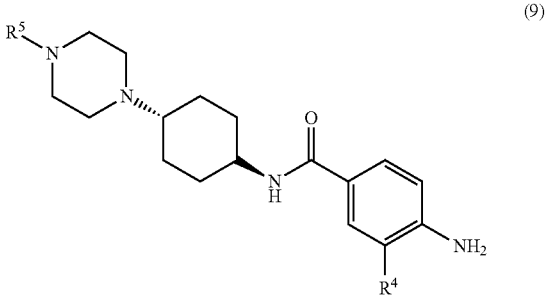
(9)

wherein
R⁴ and R⁵ are as hereinbefore defined,
is reacted with a compound of formula (10)

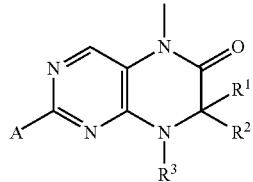
(10)

wherein R¹, R² and R³ are as hereinbefore defined and A is a leaving group,
wherein the compound of formula (9) is obtained using process step 1 and/or process step 2 and/or process step 3 as hereinbefore defined.

DEFINITION OF TERMS USED

The term "alkyl groups", including alkyl groups which are a part of other groups, denotes branched and unbranched alkyl groups with 1 to 12 carbon atoms, preferably 1 to 6 carbon atoms, most preferably 1 to 4 carbon atoms, such as, for example methyl, ethyl, propyl, butyl, pentyl, hexyl, heptyl, octyl, nonyl, decyl and dodecyl. Unless otherwise stated, the abovementioned terms propyl, butyl, pentyl, hexyl, heptyl, octyl, nonyl, decyl and dodecyl include all the possible isomeric forms. For example, the term propyl includes the two isomeric groups n-propyl and isopropyl, the term butyl includes n-butyl, iso-butyl, sec-butyl and tert.-butyl, the term pentyl includes iso-pentyl, neopentyl, etc.

In the above-mentioned alkyl groups one or more hydrogen atoms may optionally be replaced by other groups. For example these alkyl groups may be substituted by halogen, preferably fluorine, chlorine and bromine. All the hydrogen atoms of the alkyl group may optionally be replaced.

Examples of "cycloalkyl groups" are cycloalkyl groups with 3 to 8 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally also carry one or more substituents, for example OH, $NO_2$, CN, OMe, —$OCHF_2$, —$OCF_3$, —$NH_2$ or halogen, preferably fluorine or chlorine, $C_1$-$C_{10}$-alkyl, preferably $C_1$-$C_5$-alkyl, preferably $C_1$-$C_3$-alkyl, more preferably methyl or ethyl, —O—$C_1$-$C_3$-alkyl, preferably —O-methyl or —O-ethyl, —COOH, —COO—$C_1$-$C_4$-alkyl, preferably —COO-methyl or —COO-ethyl or —$CONH_2$. Particularly preferred substituents of the cycloalkyl groups are =O, OH, $NH_2$, methyl or F.

Generally, the term "halogen" denotes fluorine, chlorine, bromine or iodine, preferably fluorine, chlorine or bromine, most preferably chlorine.

The "leaving group A" denotes a leaving group such as for example —O-methyl, —SCN, fluorine, chlorine, bromine, iodine, methanesulphonyl, ethanesulphonyl, trifluoromethanesulphonyl or p-toluenesulphonyl, preferably chlorine.

The protective group "PG" denotes a protective group such as for example methyl carbamate, ethyl carbamate, 2,2,2-trichloroethyl carbamate, 2-trimethylsilylethyl carbamate, 2-chloroethyl carbamate, t-butyl carbamate, vinyl carbamate, allyl carbamate, benzyl carbamate, p-methoxybenzyl carbamate, N-formyl amide, N-acetyl amide, N-trifluoroacetyl amide, N-phenylacetyl amide, N-benzoyl amide, and benzyloxycarbonyl amide, Further usable protective groups usable to protect the amino group of the compound of formula (5) are described in: *Protective Groups in Organic Synthesis*, Third Edition. Theodora W. Greene, Peter G. M. Wuts, 1999 John Wiley & Sons, Inc., Chapter 7 p 494-653;

PREFERRED EMBODIMENTS OF THE PRESENT INVENTION

Preferred Compounds Produced

According to a preferred embodiment $R^3$ to $R^5$ are as hereinbefore defined, and $R^1$ and $R^2$ denote independently from each other a hydrogen or $C_1$-$C_3$-alkyl. More preferred $R^1$ and $R^2$ denote independently from each other a hydrogen, methyl, or ethyl. Most preferably, $R^1$ denotes hydrogen and $R^2$ denotes ethyl.

According to a preferred embodiment $R^1$, $R^2$, $R^4$ and $R^5$ are as hereinbefore defined, and $R^3$ preferably denotes hydrogen or a group selected from $C_1$-$C_3$-alkyl and $C_3$-$C_6$-cycloalkyl. More preferred $R^3$ denotes methyl, ethyl, propyl or isopropyl. Most preferably, the substituent of $R^3$ denotes isopropyl.

According to a preferred embodiment $R^1$, $R^2$, $R^3$ and $R^5$ are as hereinbefore defined, and $R^4$ preferably denotes hydrogen or a group selected from among —CN, hydroxy, $C_1$-$C_3$-alkyl, $C_1$-$C_3$-alkyloxy and $C_1$-$C_3$-alkylthio. More preferred $R^4$ denotes, methoxy, ethoxy, methylthio and ethylthio. Most preferably, the substituent of $R^4$ denotes methoxy.

According to a preferred embodiment $R^1$ to $R^4$ are as hereinbefore defined, and $R^5$ preferably denotes $C_1$-$C_4$-alkyl, $C_1$-$C_2$-alkyl-$C_3$-$C_6$-cycloalkyl or $C_3$-$C_6$-cycloalkyl.

More preferred $R^5$ denotes methyl, ethyl, propyl or —$CH_2$-cyclopropyl.

Most preferably, the substituent of $R^5$ denotes —$CH_2$-cyclopropyl.

Particularly preferred compounds of formula (11) which may be manufactured according to the process of the present invention with regard to especially preferred groups of $R^1$, $R^2$, $R^3$, $R^4$ and $R^5$ are disclosed in prior art documents WO 2006/018220 A2 and WO 2004/076454 A1, the whole disclosure of both documents is incorporated by reference, respectively, in the content of the present description.

All the groups mentioned in the definition of $R^1$ to $R^5$ may optionally be branched and/or substituted.

Within the meaning of the present invention, the compounds of general formula (5), (6), (8), (9) or (11) produced according to the processes of the present invention may be optionally in form of its tautomers, racemates, enantiomers, diastereomers and the mixtures thereof and optionally in form of the salts. The compounds of general formula (11) also embrace the physiologically acceptable or pharmacologically acceptable salts, solvates, hydrates or polymorphs thereof. The compounds of formula (5), (6), (8) and (9) represent important intermediate products for preparing the compounds of formula (11).

The compounds produced according to the invention may be prepared by synthesis methods described hereinafter, while the substituents of general formulae (3) to (11) have the meanings given hereinbefore. In case a number of steps, for example 2 steps, are combined, the product of every step may be purified according to known processes, preferably recrystallisation, respectively, or the obtained product may be used as such in the subsequent step.

Preferred Methods of Production

Step 1

According to Step 1, a compound of formula (3) is reacted with a compound of formula (4) to obtain a compound of formula (5) (see Diagram 1). Compound (3) and compound (4) are either commercially available or may be prepared by procedures known from the chemical literature.

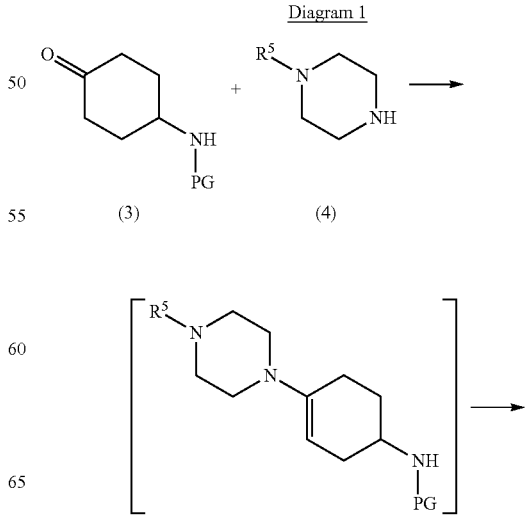

Diagram 1

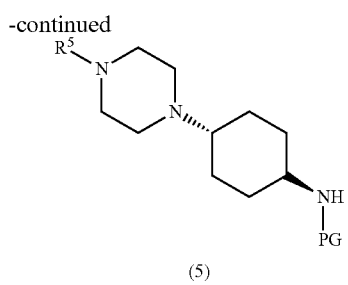

(5)

In Step 1, the compound (3), an aminocyclohexanone wherein the nitrogen atom is protected by a protecting group PG, is reacted with the heterocyclic compound of general formula (4) in a suitable solvent or mixture of solvents. The reaction is preferably conducted under reflux. The resulting enamine is then hydrogenated with a metal catalyst, preferably, Pt catalyst, preferably selected from Pt/C and platinum-IV-oxide (PtO$_2$), most preferably platinum-IV-oxide (PtO$_2$), in an appropriate solvent, like THF, toluene, ethanol, methanol, ethylacetate and mixtures thereof under a suitable hydrogen pressure, e.g. between 30 and 60 psi. The reaction is usually performed at a temperature above room temperature, for example, in the range of 35° C. to 65° C. Then the catalyst is removed. The reaction product in form of a mixture of the cis- and trans-form (free base) is obtained and may be worked up as usual (e.g. addition of water and subsequently diluted acid such as aqueous hydrochloric acid). The cis- and trans-compounds are separated by cristallisation out of water. For example, the crude product may be recrystallised from a suitable solvent in order to obtain the pure trans-product.

In the process as known from prior art, for example WO 2006/018220, the reductive amination of the enamine is performed with NaBH$_4$ as source of hydrogen and subsequently hydrochloric acid is added. However, the use of the sodium boronhydride reagent leads to potential disadvantages, which might result in an inhomogeneous reaction process, with decreased yield and side-products.

In the present step 1 according to the invention and in contrast to the prior art process a heterogeneous catalytical method with hydrogen is performed. It has been found that a suitable catalyst is a metal catalyst, pereferably a Pt catalyst. Preferable catalysts are Pt/C and platinum-IV-oxide (PtO$_2$). Most preferred is platinum-IV-oxide (PtO$_2$). The solvent is preferably an aprotic organic solvent, for example, dichloromethane, acetone, ethylene glycol dimethyl ether, diglyme, toluene, tetrahydrofuran (THF), preferably toluene or THF, most preferably toluene. A preferred solvent is also an alcohol such as ethanol, methanol, isopropanol, n-propanol, n-butanol and/or tert.-butanol, most preferably ethanol or methanol. More preferably the solvent is a mixture of an aprotic solvent and an alcohol. Preferably the solvent is a mixture of toluene and an alcohol. Particularly use is made of a toluene/ethanol mixture. The ratio of the mixture of toluene/alcohol, preferably toluene/ethanol is preferably adjusted in the range from about 4-5:1. Present step 1 allows for a significantly improved ratio of trans-compound:cis-compound which is about 3:1. Therefore, a stereoselective reductive amination is achieved. The best results are obtained with platinum-IV-oxide as catalyst in a mixture of toluene/ethanol, preferably in the range from about 4-5:1. Thus an isolated yield of >50% (trans-isomer) can be achieved. Other catalysts like Pd/C or Raney-Ni hydrogenate the enamine as well, with trans/cis ratios as shown in the following table:

TABLE

| | Catalyst | | | | | | |
|---|---|---|---|---|---|---|---|
| | Pt/C 5% | Pt/C 5% | Pd/C 5% | Ra.—Ni | PtO$_2$ 1% | PtO$_2$ 1% | Pt/C 5% |
| Solvent | THF | Ethanol | Ethanol | Ethanol | Ethanol | THF | Toluene/Ethanol (4:1) |
| trans:cis ratio | 45:55 | 44:56 | 36:64 | 19:81 | 60:40 | 60:40 | 48:52 |
| isolated yield (trans) | 33% | 23% | 23% | — | — | — | — |

Step 2

According to Step 2, in compound (5) obtained in Step 1 the protecting group is removed to obtain compound (6) (see Diagram 2).

Diagram 2

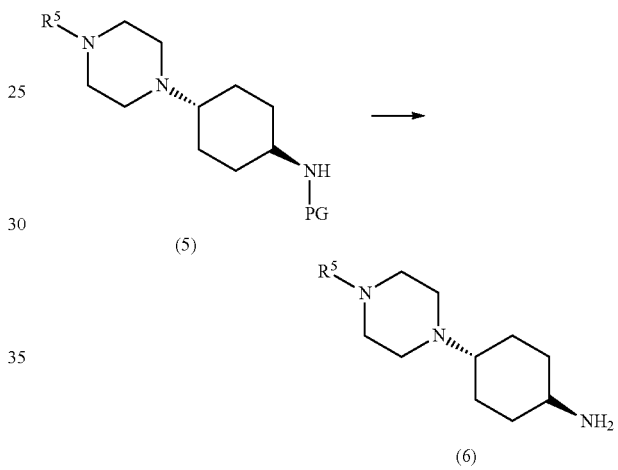

The cleavage of a protecting group PG is a procedure well known in the prior art. Usually, the amino-protecting group PG can be any suitable amino-protecting group that is known in the art. Typical examples of protecting groups have already been described above such as tert-butyloxycarbonyl (Boc), acetyl and formyl. The step of cleaving the nitrogen protecting group is generally accomplished by well known techniques in prior art. Usually an acidic hydrolysis with an organic or inorganic acid is used such as HCl, H$_2$SO$_4$, TFA, AcOH, MeSO$_3$H or TsOH in a variety of protic or polar nonprotic solvents such as alcohols, ethers or dichloromethane (DCM). However, in the process of prior art the removal of the protecting group is usually accomplished with hydrochloric acid under reflux for several hours. The resulting amine is isolated as its HCl salt. The problem of this process is the potential formation of impurities because the hydrochloric acid can react with substituents present at the heteroatom.

In the process step 2 according to the present invention the formation of this impurity is circumvented. The acidic hydrolysis is performed using p-toluenesulfonic acid (tosic acid, TsOH) as non-nucleophilic acidic reagent for cleavage of the protecting group. This kind of non-nucleophilic acidic reagent does not react with any substituent under decomposition of the compound in an undesired side-reaction. Preferably protecting groups used in step 2 according to the present invention are acetyl, formyl, trifluoracetyl, ethoxycarbonyl, tert.-butoxycarbonyl, benzyloxycarbonyl, benzyl, methoxybenzyl or 2,4-dimethoxybenzyl group. The product in step 2 is therefore a crystalline tritosylate salt which is usually obtained in good yield.

Step 3

According to Step 3, the compound of formula (6) obtained in Step 2 is reacted with a compound of general formula (7) to obtain a compound of general formula (8) (see Diagram 3).

Diagram 3

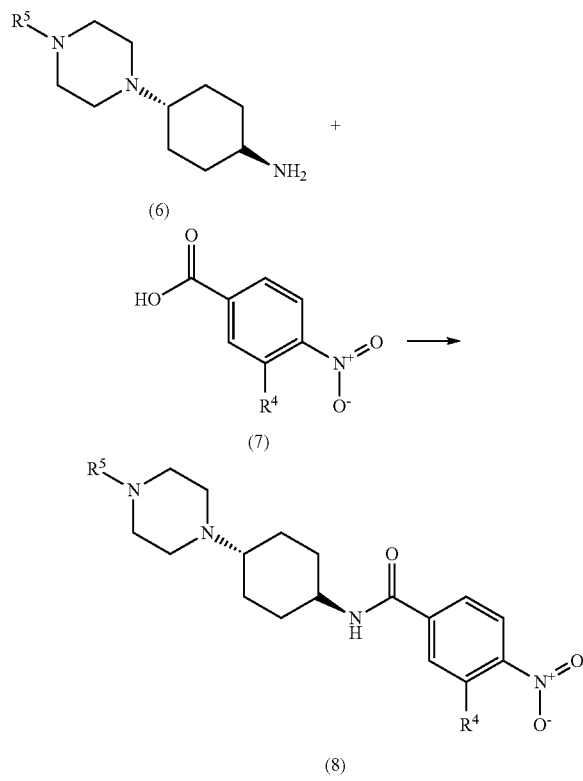

In Step 3, the benzoic acid compound (7), optionally at first converted into an acyl halide compound, is reacted with the amine compound of formula (6) using a base and a solvent. The reaction is usually performed at a temperature which is above room temperature, preferably in the range of 35° C. to 75° C. The reaction product (compound (8)) precipitates and is then worked up as usual. The obtained compound (6) may be purified by chromatography or by crystallisation or used as the crude product in the subsequent Step 4 of the synthesis.

In the process according to prior art the base commonly used is N-ethyldiisopropyl-amine (Hunigsbase) and the solvent commonly used is THF. It has been found that the use of an alkali or alkaline earth hydroxide as base such as NaOH or KOH instead of N-ethyldiisopropylamine as base and a protic solvent such as water instead of the aprotic solvent THF is advantageous. Surprisingly the yield can be significantly increased from 83 to 97%.

Step 4

According to Step 4, the compound of formula (8) obtained in Step 3 is hydrogenated to form the compound of formula (9) (see Diagram 4). This step may be carried out using methods known from the chemical literature.

Diagram 4

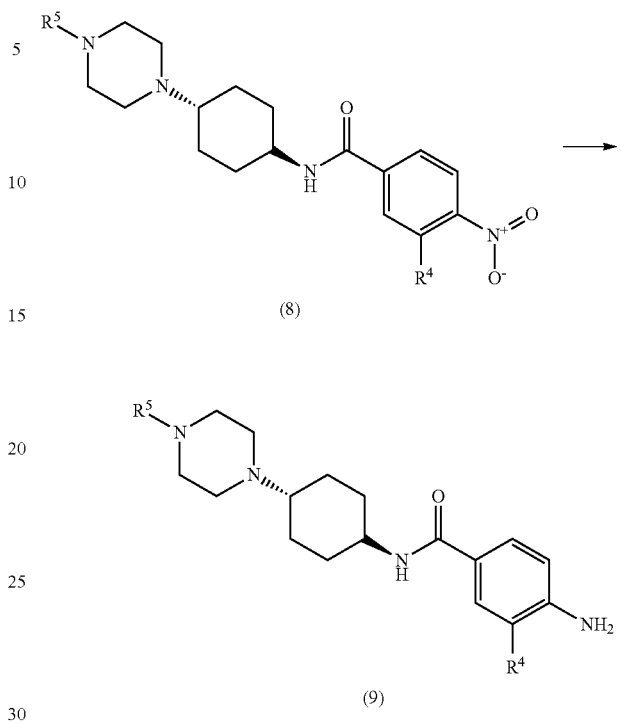

In Step 4, the compound of formula (8) is hydrogenated using a catalyst in a solvent under a suitable hydrogen pressure (20-100 psi), preferably in the range of 30 to 60 psi. The hydrogenation reaction is usually performed at a temperature which exceeds room temperature, for example in the range of 40 to 70° C. The catalyst may be any catalyst known from prior art, particularly preferred is Raney-Nickel. After completion of the reaction the catalyst is removed. The obtained compound of formula (9) may be purified or used as such in the next step without further purification.

Step 5

According to Step 5, the reaction of the compound of formula (9) obtained in Step 4 to yield the compound of formula (11) (Diagram 5) may be carried out using methods known from the chemical literature, for e.g. in WO 2009/019205; WO 2007/090844, WO 2006/021378, WO 2006/018220 and 2004/076454.

Diagram 5

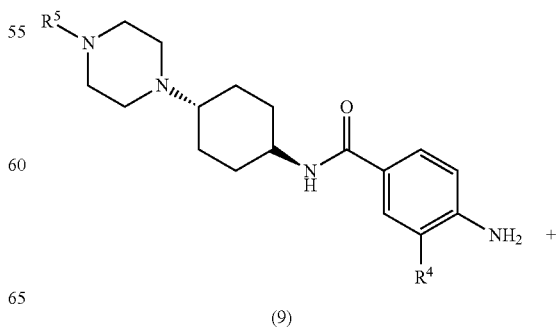

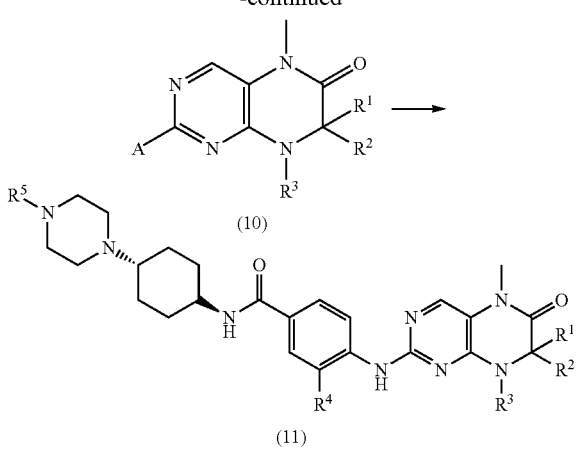

(10)

(11)

For example, in step 5, compound of formula (10) and compound of formula (9) are stirred with acid, for example hydrochloric acid or tosic acid, in a solvent, for example ethanol, propanol, butanol, pentanol, 4-methyl-2-pentanol at reflux temperature for several hours. The precipitated product (11) is separated and worked up as ususal, optionally washed with water, and dried. The obtained compound (11) may be purified by chromatography or by crystallisation.

As a matter of course any of the above-described steps may be used isolated or two or several steps may be combined to obtain the desired reaction products.

Optimum reaction conditions and reaction times for each individual step may vary depending on the particular reactants employed. Unless otherwise specified, solvents, temperatures and other reaction conditions may be readily selected by one of ordinary skill in the art. Specific procedures are provided in the Synthesis Example section. Typically, reaction progress may be monitored by high pressure liquid chromatography (HPLC) if desired. Intermediates and products may be purified by crystallization. Unless otherwise described, the starting materials and reagents are either commercially available or may be prepared by one skilled in the art from commercially available materials using methods described in the chemical literature.

Synthesis Example

Abbreviations

EtOH ethanol
MeOH methanol
THF tetrahydrofuran
p-TsOH p-toluenesulfonic acid

Synthesis of Compound (11a)

For the sake of completeness, a process for the manufacture of the compound of general formula (11a) is described hereinafter in detail.

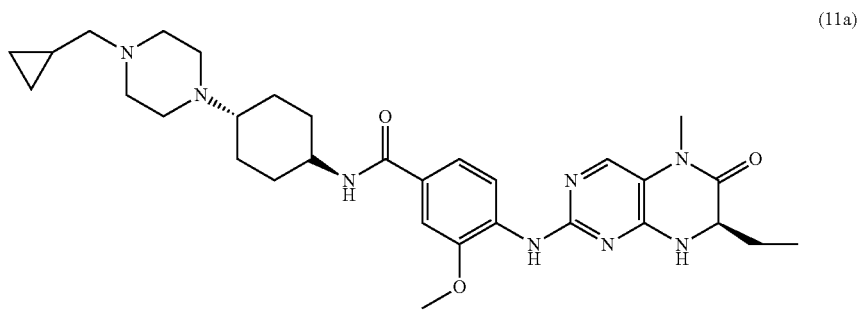

(11a)

The following method is to be understood as an illustration of the invention without restricting it to the subject matter thereof. In the following scheme 1 the reaction step 1 to step 5 are shown in detail.

Scheme 1a

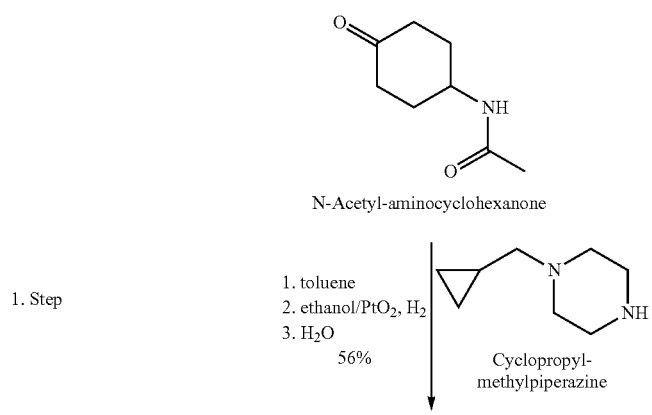

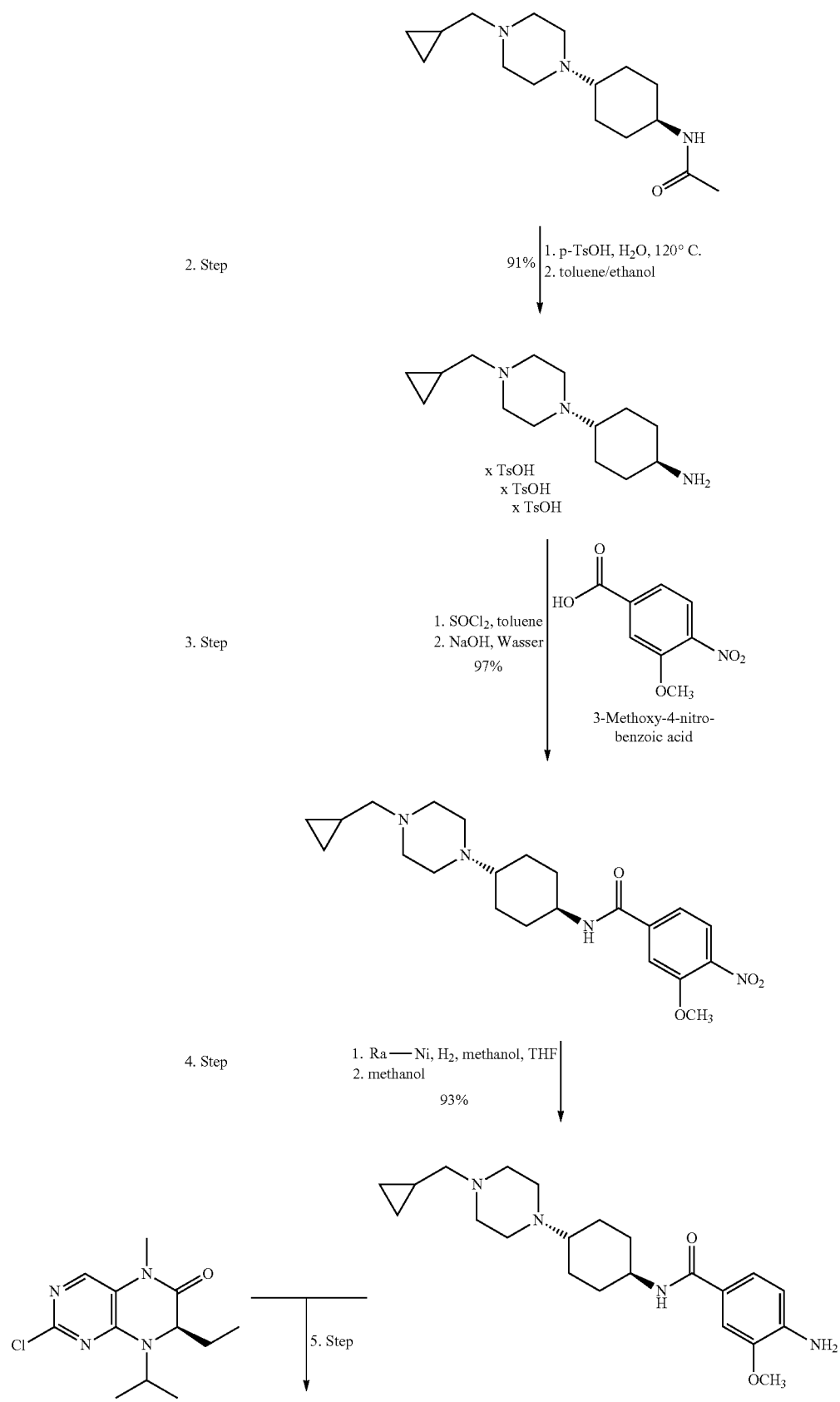

-continued

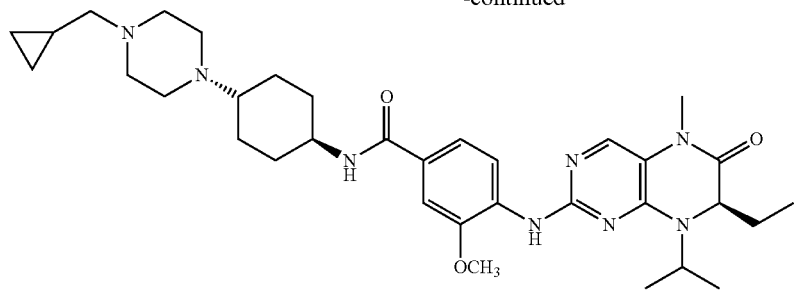

Step 1

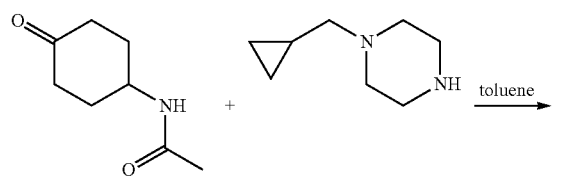

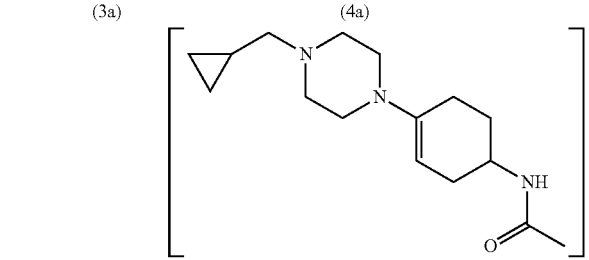

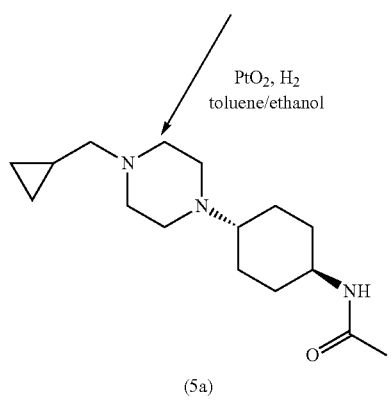

A mixture of 100.0 g (644.4 mmol) of compound (3a), namely N-acetyl-aminocyclohexanone, 1.0 L toluene, and 99.4 g (708.8 mmol) cyclopropylmethyl-piperazine compound (4a) was heated to reflux. Under reflux water was removed by a water separator, and additional 35 mL of toluene were distilled off. After completion of the reaction, the reaction mixture was cooled to 70° C., and 200 mL of ethanol were added. The solution containing the enamine was hydrogenated at 50 psi in presence of 1.00 g PtO$_2$ at 50° C. After complete conversion, the catalyst was filtered off, and the cake was rinsed with 275 ml toluene. The toluene was partly removed by distillation. To the residue 600 ml water were added at 50° C. followed by the addition of 83.0 g (68.31 mmol) aqueous HCl. To the separated aqueous layer 59.3 g (74.10 mmol) aqueous NaOH (50%) dissolved in 60 ml water were added. After addition crystallisation occurred. The suspension was cooled to 20° C. within 1.5 hours. The product was collected by filtration, washed twice with 75 ml water each, and dried under vacuum at 50° C.

Yield: 101.0 g (56.1%) of piperazin compound (5a).

Recrystallisation:

A mixture of 100.0 g piperazin compound (5a) (357.9 mmol) and 800 ml water was heated to reflux. The resulting solution was cooled to 20° C. within 2.5 hours. The suspension was stirred for additional 30 minutes at 20° C. The product was collected by filtration, washed twice with 100 ml water each, and dried under vacuum at 50° C.

Yield: 79.0 g (79.0%) of piperazin compound (5a).

Step 2

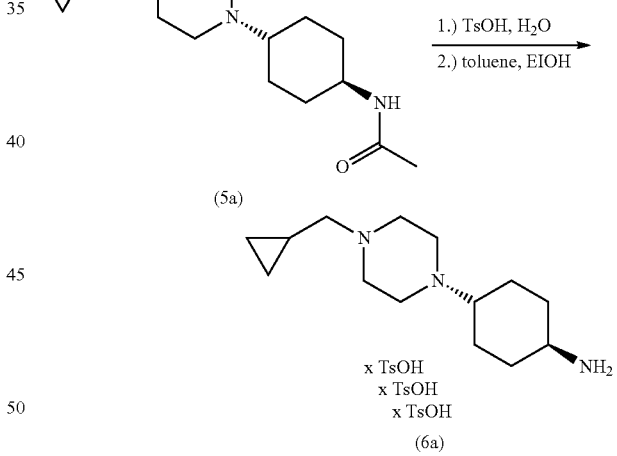

A slurry of 20.0 g (71.57 mmol) piperazin compound (5a), 68.08 g (357.8 mmol) tosic acid, and 25 ml water was heated up to 120° C. in a sealed reactor for 6 hours. After complete conversion, 120 ml toluene were added, and the biphasic mixture heated up to reflux. 29 ml of water were removed by azeotropic distillation. To the biphasic mixture 150 ml ethanol were added, and 100 ml of solvent were distilled off. The resulting suspension was cooled to 0° C. and stirred for an additional hour at 0° C. The product was collected by filtration, washed twice with 40 ml toluene/ethanol mixture each, and dried under vacuum at 50° C.

Yield: 49.15 g (91.0%) of amine compound (6a).

Step 3

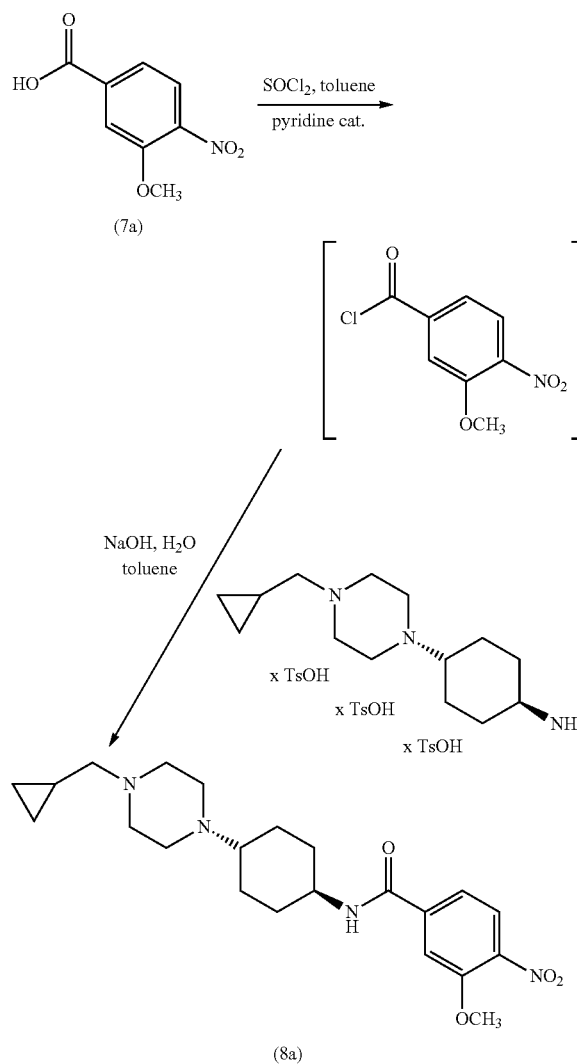

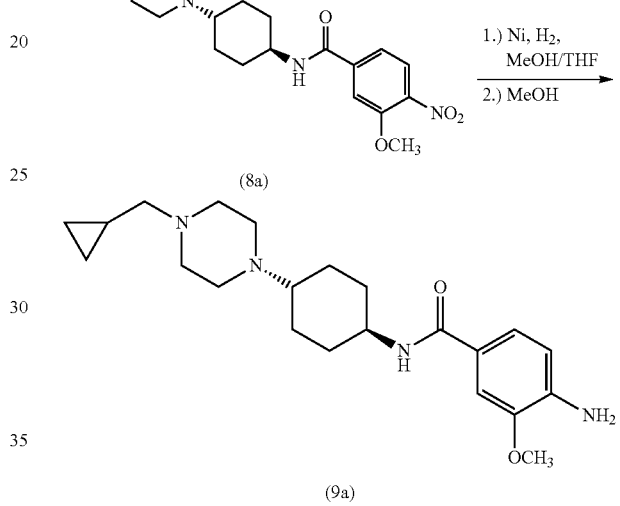

To a suspension of 11.5 g (58.36 mmol) 3-methoxy-4-nitrobenzoic acid (compound (7a)) in 82 ml toluene 116 μL pyridine were added, and heated up to reflux. Upon reflux 7.60 g (63.88 mmol) thionyl chloride dissolved in 38 ml toluene were added within 30 minutes. The mixture was stirred for an additional hour at reflux. After completion of the reaction, the resulting solution was added to a mixture of 40.0 g of amine compound (6a) (53.05 mmol), 74 ml water and 247 mmol NaOH at 60° C. The product precipitated immediately during addition. The suspension was cooled to 20° C. within one hour and stirred for an additional hour at 20° C. The product was collected by filtration, and washed twice with 100 ml water each. The product was dried at 45° C. to constant weight.

Yield: 21.49 g (97%) of amide compound (8a).

Recrystallisation:

10.0 g (24.0 mmol) of amide compound (8a) were dissolved in 60 ml ethanol under reflux. The solution was cooled to 20° C. The suspension was stirred for an additional hour at 20° C. The product was collected by filtration, and washed with 15 ml ethanol.

The product was dried at 45° C. to constant weight.

Yield: 9.09 g (91%) of amide compound (8a).

Step 4 (According to Prior Art)

20.0 g (48.02 mol) of amide compound (8a) were dissolved in a mixture of 80 ml methanol and 100 ml tetrahydrofuran. After addition of 20 g Raney-Nickel, the mixture was hydrogenated at 50 psi and 60° C. After complete conversion, the catalyst was filtered off, and the cake was rinsed with 40 ml methanol. 140 ml of solvent were removed in vacuo. To the residue 140 ml methanol were added. The suspension was refluxed until a clear solution was obtained. The solution was cooled to 2° C. The resulting suspension was stirred for an additional hour. The product was collected by filtration, and washed with 60 ml methanol. The product was dried at 60° C. to constant weight.

Yield: 17.30 g (93.0%) of aniline compound (9a).

Step 5 (According to WO 2006/018220)

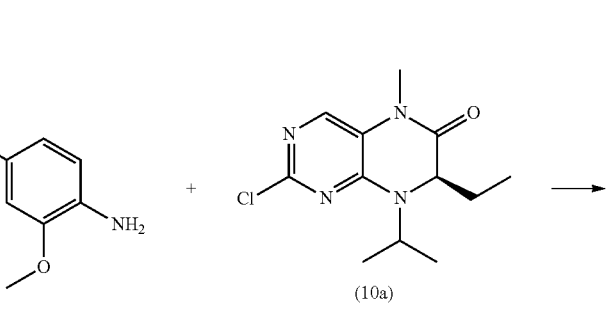

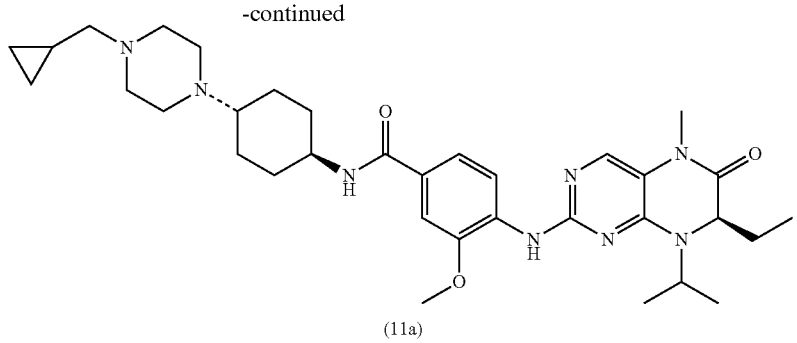

(11a)

A solution of 23 g (59.5 mmol) (9a), 16.8 g (62.5 mmol) (10a) and 28.3 g (149 mmol) para-toluenesulphonic acid hydrate in 350 mL 2-methyl-4-pentanol is refluxed for 22 hours using the water separator. After the addition of 1 g of (10a) the mixture is refluxed for a further 2 hours. 300 mL solvent are distilled off and the viscous oil is allowed to cool to 60° C. 300 mL methylene chloride and 300 mL demineralised water are added and the pH is raised by adding approx. 20 mL of 10 normal sodium hydroxide solution to pH=9. The organic phase is washed twice with demineralised water and dried over sodium sulphate. The solvent is evaporated off under reduced pressure and the residue is dissolved at 65° C. in 200 mL ethyl acetate. The mixture is left to cool slowly to 20° C., the precipitate is suction filtered and washed with cold ethyl acetate. After drying at 60° C. in the vacuum drying cupboard 24.4 g product (11a) is obtained (m.p.=182° C., DSC: 10 K/min, additional endothermic effects in the DSC diagram before melting).

The invention claimed is:

1. A process for manufacturing of a compound of formula (5)

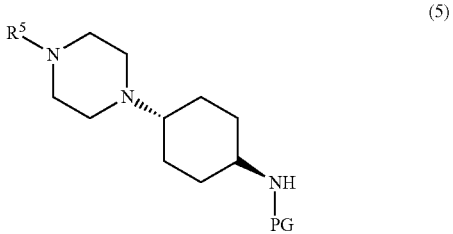

(5)

wherein
$R^5$ denotes $C_1$-$C_6$-alkyl, $C_1$-$C_4$-alkyl-$C_3$-$C_{10}$-cycloalkyl or $C_3$-$C_{10}$-cycloalkyl,
comprising
reacting a compound of formula (3)

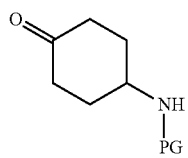

(3)

wherein PG is a protecting group with a compound of formula (4)

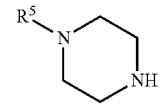

(4)

wherein
$R^5$ is as hereinbefore defined,
via an enamine intermediate which is hydrogenated in the presence of a metal catalyst and a solvent or a mixture of solvents.

2. A process for manufacturing a compound of formula (6)

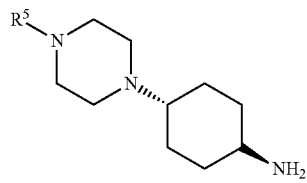

(6)

wherein
$R^5$ denotes $C_1$-$C_6$-alkyl, $C_1$-$C_4$-alkyl-$C_3$-$C_{10}$-cycloalkyl or $C_3$-$C_{10}$-cycloalkyl,
comprising removing by acidic hydrolysis the protecting group PG in a compound of formula (5)

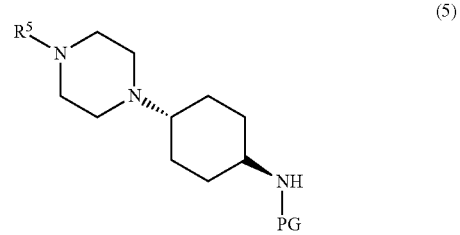

(5)

wherein
$R^5$ and PG are as hereinbefore defined, to produce the compound of formula (6).

3. A process for manufacturing a compound of formula (8)

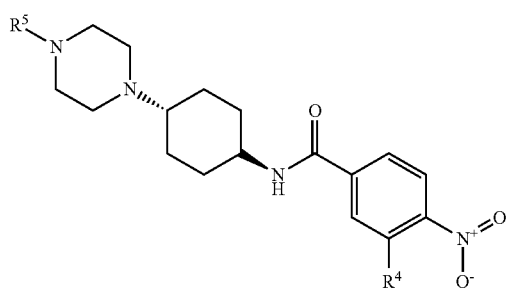
(8)

wherein $R^5$ denotes $C_1$-$C_6$-alkyl, $C_1$-$C_4$-alkyl-$C_3$-$C_{10}$-cycloalkyl or $C_3$-$C_{10}$-cycloalkyl, $R^4$ denotes hydrogen or a group selected from among —CN, hydroxy, $C_1$-$C_6$-alkyl, $C_1$-$C_5$-alkyloxy and $C_1$-$C_6$-alkylthio, comprising reacting a compound of formula (7)

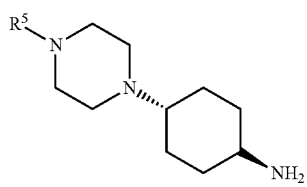
(7)

wherein $R^4$ is as hereinbefore defined, and wherein (7) is optionally converted into an acyl halide compound, with the amine compound of formula (6)

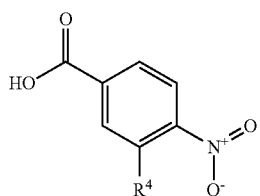
(6)

wherein $R^5$ is as hereinbefore defined, using an alkali or alkaline earth hydroxide as base, and a protic solvent.

4. A process for manufacturing a compound of formula (9)

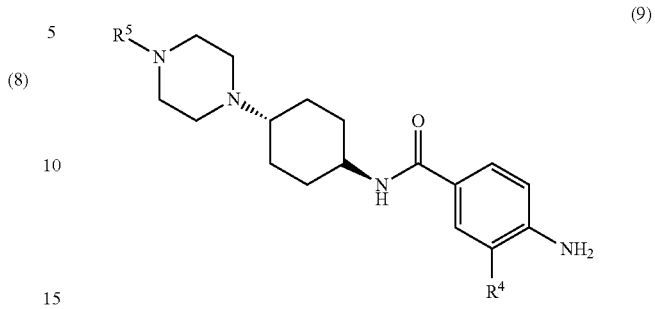
(9)

wherein $R^4$ denotes hydrogen or a group selected from among —CN, hydroxy, $C_1$-$C_6$-alkyl, $C_1$-$C_5$-alkyloxy and $C_1$-$C_6$-alkylthio, and $R^5$ denotes $C_1$-$C_6$-alkyl, $C_1$-$C_4$-alkyl-$C_3$-$C_{10}$-cycloalkyl or $C_3$-$C_{10}$-cycloalkyl, comprising 1) reacting a compound of formula (3)

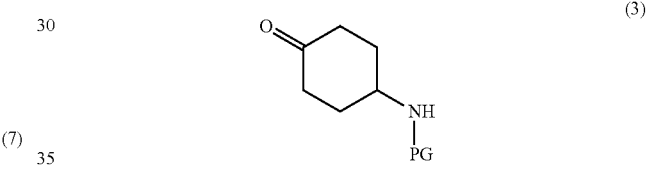
(3)

wherein PG is a protecting group with a compound of formula (4)

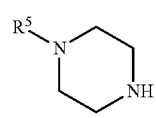
(4)

wherein $R^5$ is as hereinbefore defined, via an enamine intermediate which is hydrogenated in the presence of a metal catalyst and a solvent or a mixture of solvents to produce

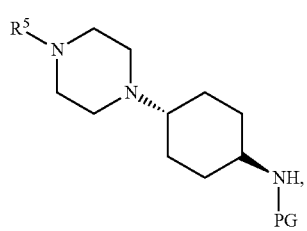
(5)

2) removing by acidic hydrolysis using p-toluenesulfonic acid (TsOH) the protecting group PG in a compound of formula (5) to produce (6)

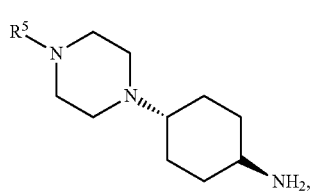
(6)

3) reacting a compound of formula (7)

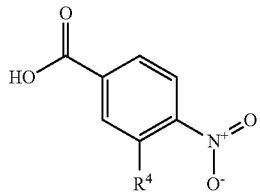
(7)

wherein (7) is optionally converted into an acyl halide compound, with the amine compound of formula (6)

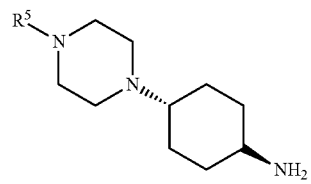
(6)

using an alkali or alkaline earth hydroxide as base, and a protic solvent, to obtain

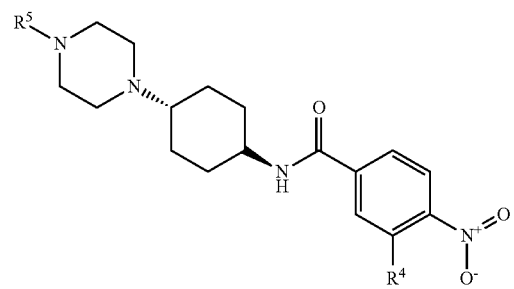
(8)

and
4) the compound of formula (8) is hydrogenated to obtain a compound of formula (9).

5. A process for manufacturing a compound of formula (11)

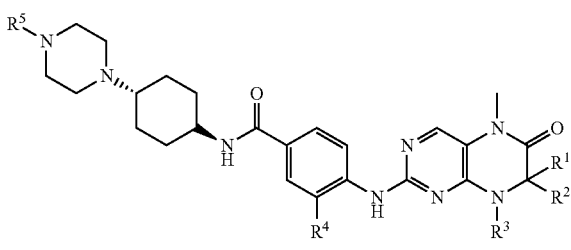
(11)

comprising
reacting a compound of formula (9)

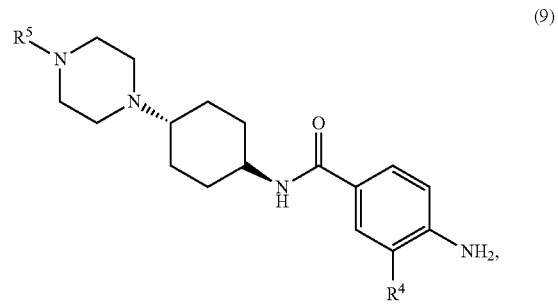
(9)

with a compound of formula (10)

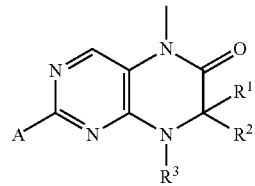
(10)

wherein A is a leaving group,
to obtain a compound of formula (11),
wherein $R^1$ and $R^2$ denote independently from each other a hydrogen or $C_1$-$C_6$-alkyl,
$R^3$ denotes hydrogen or a group selected from $C_1$-$C_6$-alkyl and $C_3$-$C_8$-cycloalkyl,
$R^4$ denotes hydrogen or a group selected from among —CN, hydroxy, $C_1$-$C_6$-alkyl, $C_1$-$C_5$-alkyloxy and $C_1$-$C_6$-alkylthio,
$R^5$ denotes $C_1$-$C_6$-alkyl, $C_1$-$C_4$-alkyl-$C_3$-$C_8$-cycloalkyl or $C_3$-$C_8$-cycloalkyl.

6. A process for manufacturing a compound of formula (11)

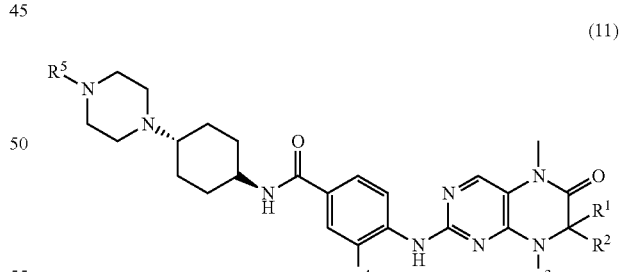
(11)

wherein
wherein $R^1$ and $R^2$ denote independently from each other a hydrogen or $C_1$-$C_6$-alkyl,
$R^3$ denotes hydrogen or a group selected from $C_1$-$C_6$-alkyl and $C_3$-$C_8$-cycloalkyl,
$R^4$ denotes hydrogen or a group selected from among —CN, hydroxy, $C_1$-$C_6$-alkyl, $C_1$-$C_5$-alkyloxy and $C_1$-$C_6$-alkylthio,
$R^5$ denotes $C_1$-$C_6$-alkyl, $C_1$-$C_4$-alkyl-$C_3$-$C_8$-cycloalkyl or $C_3$-$C_8$-cycloalkyl, comprising
hydrogenating a compound of formula (8)

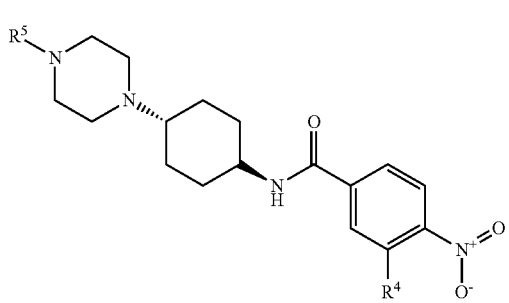

to produce

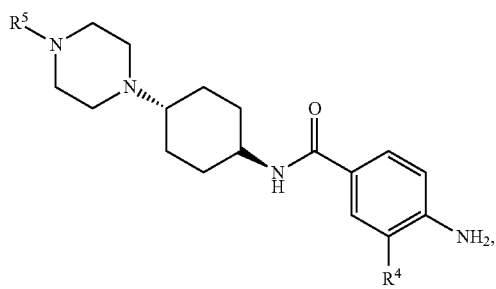

reacting a compound of formula (9)

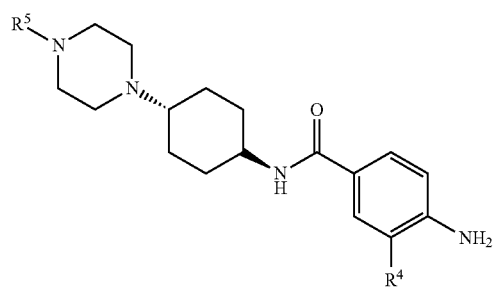

wherein
with a compound of formula (10)

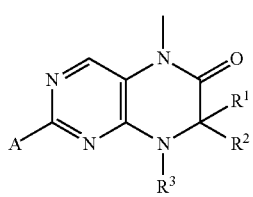

wherein A is a leaving group,
to obtain a compound of formula (11).

7. A process (step 4) for manufacturing a compound of formula (9)

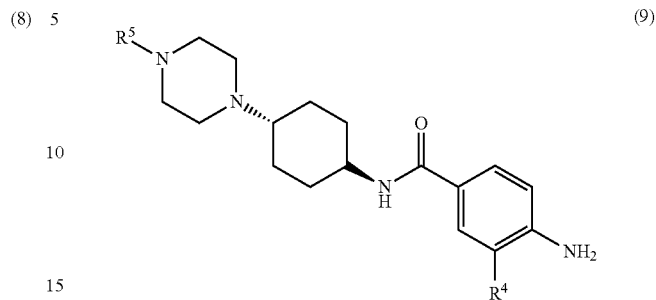

wherein
R⁴ denotes hydrogen or a group selected from among —CN, hydroxy, $C_1$-$C_6$-alkyl, $C_1$-$C_5$-alkyloxy and $C_1$-$C_6$-alkylthio,
R⁵ denotes $C_1$-$C_6$-alkyl, $C_1$-$C_4$-alkyl-$C_3$-$C_8$-cycloalkyl or $C_3$-$C_8$-cycloalkyl,
comprising hydrogenating a compound of formula (8)

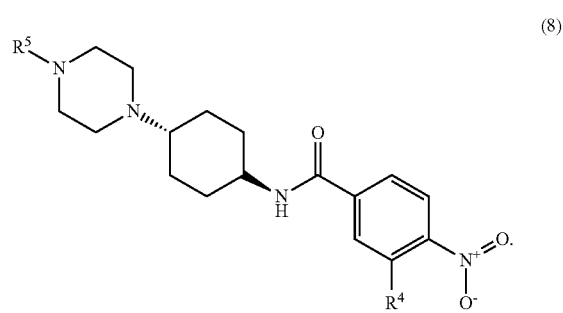

8. The process according to claim 1 wherein the metal catalyst is selected from Pt/C or platinum-IV-oxide ($PtO_2$).
9. The process according to claim 1 wherein the solvent is selected from
 an aprotic organic solvent selected from dichloromethane, acetone, ethylene glycol dimethyl ether, diglyme, toluene, tetrahydrofuran (THF),
or
 an alcohol selected from ethanol, methanol, isopropanol, n-propanol, n-butanol and/or tert.-butanol,
or
 a mixture of an aprotic solvent and an alcohol.
10. The process according to claim 9, wherein the solvent is toluene:alcohol, adjusted in the range of 4-5:1.
11. The process according to claim 4 wherein the compounds produced may be in the form of the tautomers, the racemates, the enantiomers, the diastereomers and the mixtures thereof, and optionally the salts thereof.
12. A process according to claim 1 characterized in that the metal catalyst is selected from the group consisting of a Ni catalyst, Pd catalyst or a Pt catalyst.
13. A process according to claim 12 characterized in that the metal catalyst is Pt/C or platinum-IV-oxide ($PtO_2$).

* * * * *